US00PP18402P2

(12) United States Plant Patent
Catt

(10) Patent No.: US PP18,402 P2
(45) Date of Patent: Jan. 8, 2008

(54) ***OENOTHERA* PLANT NAMED 'LISHAL'**

(50) Latin Name: ***Oenothera* Sp.**
Varietal Denomination: LISHAL

(76) Inventor: Peter Catt, Petersfield Road, Greatham Liss, Hampshire (GB), GU33 GHA ( * ) Notice: Subject to any disclaimer, the term of this patent is extended or adjusted under 35 U.S.C. 154(b) by 108 days.

(21) Appl. No.: 11/412,357

(22) Filed: Apr. 26, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell

(57) ABSTRACT

A new cultivar of *Oenothera* plant named 'LISHAL' which is an herbaceous perennial with upright stems arising from a basal rosette or crown, whose foliage is variegated, with cream margins, and whose flowers appear as terminal corymbs and are bright yellow and cup shaped. In combination these traits set 'LISHAL' apart from all other existing varieties of *Oenothera* known to the inventor.

2 Drawing Sheets

Genus: *Oenothera* sp.
Denomination: 'LISHAL'.

BACKGROUND OF THE INVENTION

The present invention relates to a new and distinct variety of evening primrose which may be grown as a perennial plant in regions where it is hardy and as an annual bedding plant in regions where it is tender. The new cultivar is known botanically as *Oenothera* and will be referred to hereinafter by the cultivar name 'LISHAL'.

The new cultivar 'LISHAL' was discovered in 2000 at a nursery in Hampshire, England as a naturally occurring branch sport on an individual whole plant of *Oenothera* 'Crown Imperial' (unpatented). The parent of 'LISHAL' is an individual plant of *Oenothera* 'Crown Imperial'. The inventor has been unable to determine the nomenclature of the species of *Oenothera* 'Crown Imperial' since it does not closely resemble any variety or species of *Oenothera* known to the inventor.

The inventor discovered 'LISHAL' while taking cuttings from plants of *Oenothera* 'Crown Imperial' for subsequent propagation and production. Whereas the foliage of *Oenothera* 'Crown Imperial' is uniformly plain deep green in color, the leaves of the branch sport, 'LISHAL' were observed by the inventor to have a cream colored margin. The inventor considered that the branch sport may have commercial potential if it could be successfully asexually propagated and found to reproduce true to type. In 2001, the inventor excised the branch sport from its parent and took an internodal stem cutting from the excised plant material. The cutting was placed under mist on a heated bench, with bottom heat temperature of 21° Centigrade. The cutting rooted and was transplanted into a 9 cm container and was observed by the inventor. The inventor observed that the new plant possessed the characteristic cream colored margin of the originally discovered branch sport, 'LISHAL'.

Since 2001, the inventor has carried out annual cycles of asexual propagation using stem cuttings and has determined that 'LISHAL' has remained stable and has reproduced true to type in successive generations of asexual reproduction.

The new cultivar 'LISHAL' is characterized by a basal rosetted crown with stiff upright stems and variegated foliage. The stems terminate with a corymb of bright yellow flowers. The foliage of 'LISHAL' remains evergreen in USDA Hardiness Zones 7 and higher, and dies back to the ground in colder regions.

The closest comparison plant known to the inventor is the parent cultivar *Oenothera* 'Crown Imperial' which may be distinguished as follows: Whereas the foliage of 'Crown Imperial' is uniformly and consistently plain deep green, the foliage of 'LISHAL' is variegated, namely mid green with a cream edge or margin.

The inventor filed an application for a grant of European Community Plant Variety Rights on Jul. 19, 2004, Ser. No. 2004/1385. The first plants of 'LISHAL' to be sold or offered for sale took place on or after May 1, 2005, by the inventor and from plants which had been growing at the inventor's nursery.

SUMMARY OF THE INVENTION

The following traits have been repeatedly observed and represent the distinguishing characteristics of the new variety 'LISHAL'. In combination these traits set 'LISHAL' apart from all other *Oenothera* known to the inventor. 'LISHAL' has not been tested under all possible conditions and phenotypic differences may be observed with variations in environmental, climatic and cultural conditions, however, without any variance in genotype.

1. 'LISHAL' is an herbaceous perennial with upright stems arising from a basal rosette or crown.
2. The foliage of 'LISHAL' is variegated, with cream margins.
3. The flowers of 'LISHAL' appear as terminal corymbs and are bright yellow and cup shaped.
4. 'LISHAL' is suitable for use in borders or in planted containers.
5. 'LISHAL' can be propagated from internodal stem cuttings which may be rooted under mist with moderate bottom heat.

BRIEF DESCRIPTION OF THE DRAWINGS

The accompanying color drawings labeled

The drawing labeled FIG. 1 depicts a clump of two year old plants of 'LISHAL' which are just coming into bud and which exhibit the characteristic cream margin to the foliage. The plants are growing in loamy garden soil out of doors at the inventor's garden in Hampshire, England.

The drawing labeled FIG. 2 depicts a close-up view of the foliage and flowers of 'LISHAL' showing the characteristic cream margins to the leaves and the large bright yellow flowers.

FIG. 1 and FIG. 2 were made using conventional techniques and although colors may appear different from actual colors due to light reflectance they are as accurate as possible by conventional photography.

BOTANICAL DESCRIPTION OF THE PLANT

Figure 1:
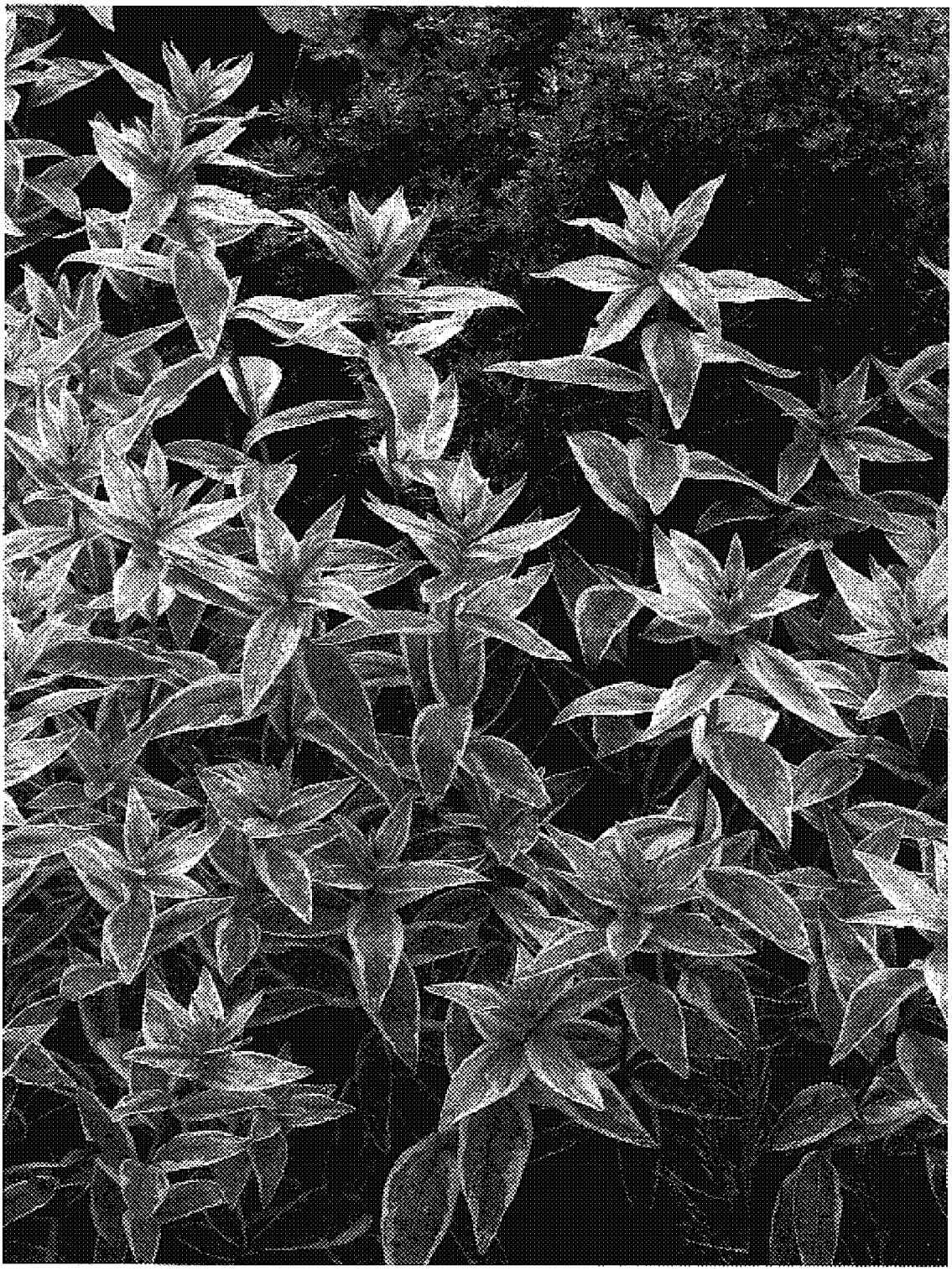
FIG. 1 and FIG. 2 illustrate the overall appearance of the new *Oenothera* cultivar 'LISHAL' showing the colors as true as it is reasonably possible to obtain in colored reproductions of this type. Colors in the drawings may differ from the color values cited in the detailed botanical description, which accurately describe the actual colors of the new variety 'LISHAL'.
Figure 2:
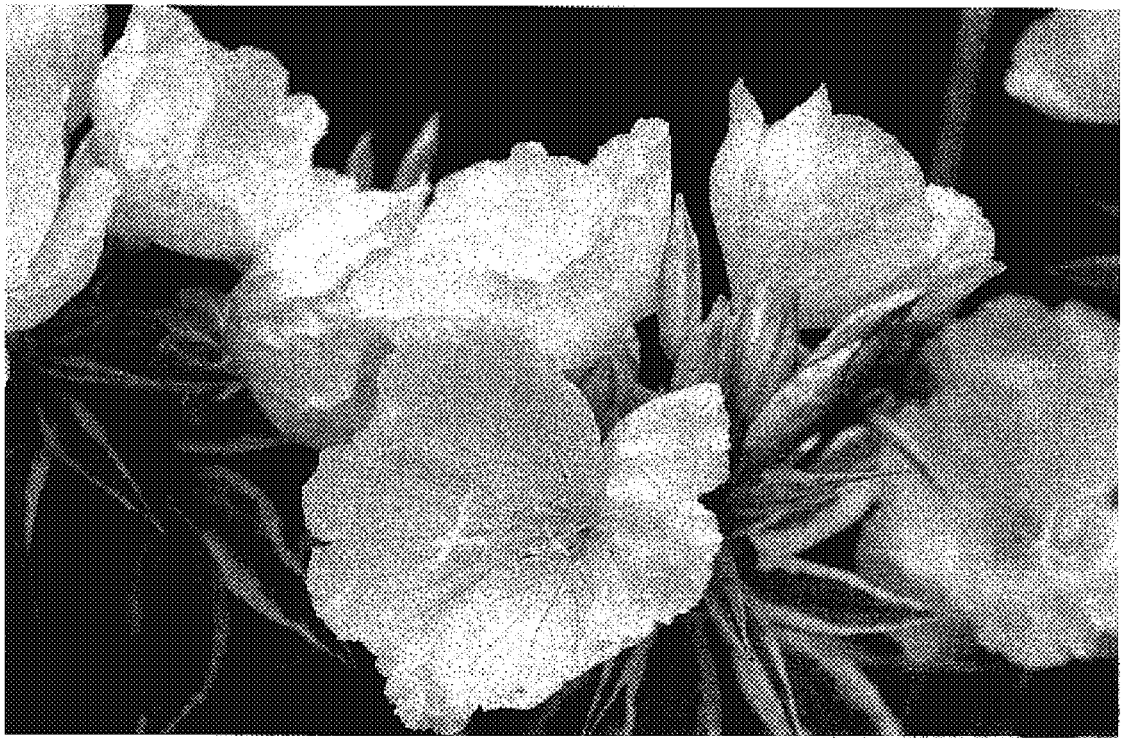

The following is a detailed description of the new *Oenothera* plant named 'LISHAL'. Data was collected in England from a 2 year old plant grown out-of-doors in a 3-liter container in Hampshire, England. The color determinations are in accordance with the 2001 edition of The Royal Horticultural Society Colour Chart, except where general color terms of ordinary dictionary significance are used.

Botanical classification: *Oenothera* 'LISHAL'.
Genus: *Oenothera.*
Species: Not known.
Denomination: 'LISHAL'.
Common name: Evening primrose.
Commercial classification: Herbaceous perennial.
Plant form: Basal rosette or crown with many upright stems. Vase shaped.
Plant use: Suitable for use in borders or in planted containers.
Cultural requirements: Fertile well-draining soil, full sun or partial shade, and minimal to moderate water.
Root system: Fine and fibrous.
Vigor: Vigorous, spreading freely by rhizomes.
Parentage: *Oenothera* 'LISHAL' was discovered as a naturally occurring branch sport on an individual whole plant of the following parent:
*Parent plant.*—*Oenothera* 'Crown Imperial'.
Plant description:
*Seasonal interest.*—Flowers bloom in June and July.
*Plant habit.*—Non-invasive evergreen basal rosette with herbaceous flowering stems.
*Dimensions.*—56 cm in height, 56 cm in width at maturity.
*Hardiness.*—Foliage is hardy and evergreen in the United Kingdom in temperatures equivalent to USDA Hardiness Zones 7 and higher. The hardiness of a whole plant has not been established outside the United Kingdom.
*Propagation.*—Softwood cuttings taken in June/July or division.
*Time to develop roots.*—10–14 days are needed for initial cuttings to develop roots.
*Temperature for rooting.*—Recommended air temperature for rooting is 24° Centigrade.
*Crop time.*—1 year needed to produce a finished 1-liter commercial container plant from a rooted cutting.
*Diseases and pests.*—No particular susceptibility or resistance to pests or diseases has been observed by the inventor.
Stems:
*Branching.*—Basal rosette with herbaceous flowering stems. Stems unbranched at flowering time, producing a few short laterals from the upper nodes later.
*Dimensions.*—Stem length: 50 cm–60 cm. Stem diameter: 4 mm–7 mm. Stem shape: Round. Stem color: 145B and 145C strongly tinged with 180A when exposed to direct sunlight. Stem pubescence: Weak. Lenticels: Absent. Internode length: 30 mm.
Foliage:
*Leaf.*—Dimensions: 79 mm in length, 28 mm in width. Shape: Obovate tending to elliptic. Arrangement: Alternate. Margins: Sparsely denticulate. Division: Entire. Apex: Acute. Base: Cuneate. Color (adaxial): 137C and 146B. Broad marginal band of 5C. Irregular patches of intermediate color where two zones meet. Color (abaxial): 147C and 147D. Broad marginal band of 5D. Irregular patches of intermediate color where two zones meet. Pubescence (adaxial and abaxial): Absent Venation pattern: Pinnate. Vein color (adaxial and abaxial): 157A. Lateral veins similar to lamina. Attachment: Sessile. Stipules: Absent.
*Fragrance.*—None observed.
Flowers:
*Bloom period.*—June/July.
*Inflorescence type.*—Terminal corymb.
*Quantity of flowers per stem.*—14–21.
*Pedicel.*—Dimensions: 1 mm to 2 mm in length, 1 mm in diameter. Color: Between 150C and 150D, variably tinged with red (too small to color match). Pubescence: Sparsely glandular-pubescent.
*Bud.*—Dimensions: 42 mm to 48 mm in length, 7 mm to 8 mm in diameter. Shape: Narrowly ovoid-ellipsoid with an acute apex. Color: 9D variable tinged and veined with red (too small to color match).
*Flower.*—Greatest overall diameter: 45 mm to 68 mm. Depth of throat: Tube formed from fused basal sections of calyx and corolla, 13 mm to 16 mm in length, 2 mm in diameter. Length of perianth: Including tube, 21 mm to 30 mm. Flowers, persistent or self-cleaning: Self-cleaning. Shape: Corolla bowl-shaped above tubular hypanthodium. Aspect: Facing outward to upward. Calyx: Diameter: not applicable. The calyx opens by splitting down one side and folds over to accommodate corolla so that the shape is irregular and somewhat flattened. Height: Unclear because of form, but length approximately 20 mm. Pubescence and type: Glandular-pubescent (also hypanthodium). Color: 164C, variably tinged and veined with red giving an overall impression of between 170C and 170D. Number of sepals: Not applicable, fused.
*Petals.*—Number: 4. Fused or free: Free above the hypanthodium. Dimensions: 34 mm to 39 mm in length, 37 mm to 44 mm in width. Shape: Obcordate, upper surface concave. Margin: Upper third undulate and crenate, otherwise entire and mostly flat. Surface: Glabrous. Color (adaxial and abaxial): Outer surface between 5A and 5B. Inner surface between 5A and 5B intensifying to between 6A and 6B with age.

*Flower fragrance.*—Weak.

Reproductive organs:

*Stamens.*—Stamens: 8, inserted at the top of the hypanthodium. Filament dimensions: 13 mm in length, <1 mm in width. Filament color: 12A. Anther dimensions: 5 mm to 6 mm in length, 1 mm in width. Anther shape: Slender elongate, attached to filament at midpoint. Anther color: 12A. Pollen quantity: Copious. Pollen color: Mid-Yellow, impossible to color match satisfactorily.

*Stigma.*—Shape: 4 lobed with lobes held at right angles to style and each other. Dimensions: Lobes 9 mm in length, 1 mm wide. Color: 9A. Style dimensions: 34 mm in length, <1 mm in width. Ovary Number: 4 locules. Dimensions: 9 mm in length, 4 mm in width. Shape: Quadrangular-ellipsoid with strongly winged angles. Position: Inferior. Color: 144B strongly tinged with red on the angles (too small to color mach successfully).

Seed: No seed observed to date.

It is claimed:

1. A new and distinct cultivar of *Oenothera* plant named 'LISHAL' as described and illustrated.

* * * * *